US010605885B2

(12) United States Patent
Robinson et al.

(10) Patent No.: US 10,605,885 B2
(45) Date of Patent: Mar. 31, 2020

(54) PHASE OFFSET DETERMINATION IN MAGNETIC RESONANCE IMAGING (71) Applicant: MEDIZINISCHE UNIVERSITÄT WIEN, Vienna (AT)

(72) Inventors: Simon Robinson, Vienna (AT); Korbinian Eckstein, Vienna (AT)

(73) Assignee: MEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 16/323,653

(22) PCT Filed: Jun. 9, 2017

(86) PCT No.: PCT/EP2017/064131
§ 371 (c)(1),
(2) Date: Feb. 6, 2019

(87) PCT Pub. No.: WO2018/028855
PCT Pub. Date: Feb. 15, 2018

(65) Prior Publication Data
US 2019/0170843 A1 Jun. 6, 2019

(30) Foreign Application Priority Data
Aug. 8, 2016 (EP) ..................................... 16183228

(51) Int. Cl.
*G01V 3/00* (2006.01)
*G01R 33/565* (2006.01)
(Continued)

(52) U.S. Cl.
CPC ........ *G01R 33/56563* (2013.01); *A61B 5/055* (2013.01); *G01R 33/565* (2013.01); *A61B 5/7257* (2013.01)

(58) Field of Classification Search
USPC ......................................................... 324/307
See application file for complete search history.

(56) References Cited

U.S. PATENT DOCUMENTS 7,894,875 B2 * 2/2011 Van Zijl ................. A61B 5/055
600/410
2017/0307717 A1 * 10/2017 Geraghty ........... G01R 33/5616
2018/0011158 A1 * 1/2018 Katscher ................ A61B 5/055

FOREIGN PATENT DOCUMENTS

EP 1310211 A1 5/2003

OTHER PUBLICATIONS

Robinson et al., "Combining Phase Images From Multi-Channel RF Coils Using 3D Phase Offset Maps Derived From a Dual-Echo Scan," Magnetic Resonance in Medicine 65:1638-1648 (2011).
(Continued)

*Primary Examiner* — Rodney E Fuller
(74) *Attorney, Agent, or Firm* — Hoffmann and Baron, LLP (57) ABSTRACT The disclosed subject matter relates to a method for determining phase offsets in a complex-valued image in Magnetic Resonance Imaging, including the steps of,
immobilising an object and acquiring a first image thereof at a predetermined first echo time and a second image thereof at a predetermined second echo time, the first and second images being separated into first and second magnitude images and first and second phase images, respectively, wherein a ratio between said first echo time and said second echo time is chosen to be n:(n+1), n being a positive integer;
generating, pixel by pixel, a phase evolution image; and
subtracting, pixel by pixel, an n-fold of the phase evolution image from the first phase image to obtain a phase offset image containing said phase offsets.

12 Claims, 4 Drawing Sheets

(51) Int. Cl.
*A61B 5/055* (2006.01)
*A61B 5/00* (2006.01)

(56) References Cited

OTHER PUBLICATIONS

Robinson et al., "A Method for Unwrapping Highly Wrapped Multi-Echo Phase Images at Very High Field: UMPIRE," Magnetic Resonance in Medicine 72:80-92 (2014).
Hammond et al., "Development of a robust method for generating 7.0 T multichannel phase images of the brain with application to normal volunteers and patients with neurological diseases," NeuroImage 39, pp. 1682-1692 (2008).
Extended European Search Report dated Feb. 20, 2017.
International Search Report dated Sep. 19, 2017.
English Translation of International Preliminary Report on Patentability in corresponding International Application No. PCT/EP2017/064131.

\* cited by examiner

*Fig. 1*
(State of the Art)

PHASE OFFSET DETERMINATION IN MAGNETIC RESONANCE IMAGING

CROSS-REFERENCE TO RELATED APPLICATIONS

This application is a National Phase application of International Application No. PCT/EP2017/064131 filed Jun. 9, 2017 which claims priority to the European Patent Application No. 16 183 228.2 filed Aug. 8, 2016, the disclosures of which are incorporated herein by reference.

TECHNICAL FIELD

The disclosed subject matter relates to a method for determining phase offsets in a complex-valued image acquired in Magnetic Resonance Imaging (MRI).

BACKGROUND ART

The present invention relates to a method for determining phase offsets in a complex-valued image acquired in Magnetic Resonance Imaging (MRI).

MRI is used in radiology to visualize details of structures in a patient's body. To align the magnetic spin of the nuclei, mostly of protons in water molecules in the body tissue, the patient is placed inside a powerful static magnetic field. Excited by an electro-magnetic radio-frequency pulse from a transmitter coil, the nuclei resonating at this frequency deflect and then gradually relax towards the static field while emitting detectable electro-magnetic radiation, which can be captured as an "echo" at a certain time after excitation (the "echo time") by a receiver coil. Relaxation times and the resonance frequency of the nuclei depend both on local properties of the tissue material, which represents the underlying principle allowing visualization of these properties. The characteristics of the image are also influenced by proton density and magnetic field strength. By superposing linear magnetic field gradients in three orthogonal directions and adjusting the excitation frequency, certain volumetric regions ("volume elements") can be measured by both selective excitation and frequency analysis of the captured echo signals. Fourier-transforming the latter generates complex representations of the captured values in image space and their phases, which can be made readable.

When the excitation is performed on 2-dimensional slices through the object, they are selected by adjusting the field gradients, thereafter resonant frequency values are captured and processed, forming 2-dimensional images, a number of which can be acquired to form a 3-dimensional representation of the object. Alternatively, in 3-dimensional imaging, a large volume of tissue is excited and spatially encoded using frequency encoding in one direction and phase encoding in both of the remaining two orthogonal directions.

In the past, magnitude values have been used primarily from the complex representations. Nevertheless, phase values allow for the extraction of additional information about local properties of the tissue, where they specifically benefit from strong susceptibility effects at high magnetic field strengths. For example, phase information is used in neuro-imaging in phase-contrast angiography, Susceptibility-Weighted Imaging (SWI), susceptibility mapping—also known as Quantitative Susceptibility Mapping (QSM), Susceptibility Tensor Imaging, to depict iron accumulation in neurodegenerative disorders and to map in vivo conductivity. It can also be used to monitor temperature and encode flow velocity.

However, each phase value acquired by a receiver coil of the MRI machine is subject to a time-independent offset, often referred to as "phase offset". The phase offset comprises spatially constant components, e.g. due to the cable length from a receiver coil to a receiver, as well as spatially variable components, e.g. due to the path lengths of the excitation and echo signals from particular locations in the object to the receiver coil in question.

It has been an aim of research to determine phase offsets and subsequently eliminate their effects on Magnetic Resonance Imaging, e.g., in order to facilitate combining multiple phase images acquired with a plurality of receiver coils arranged in an array around the object and thereby increase the quality of an acquired image in terms of its signal-to-noise ratio (SNR). Several approaches have been presented in the past to determine—or at least roughly estimate—and eliminate phase offsets, whereupon a combined phase image can be generated:

One of these approaches, proposed by Roemer, P. B. et al., "The NMR phased array", Magn Reson Med 1990, 16; pp. 192-225, uses an additional body coil or other homogeneous volume reference coil, i.e., a coil which is separate from said receiver coils and has to be sensitive over (at least) all the tissue over which the receiver coils, arranged in an array around the object, are sensitive, for referencing and using a phase offset measured separately by means of the body coil for each receiver coil; however, such an additional reference coil is not commonly available in ultra-high field scanners and requires extra space and control. Moreover, inhomogeneities of the reference coil, inevitable in ultra-high field scanners, are introduced into the phase which consequently suffers both from field inhomogeneities and from the offset from the reference coil.

A different approach, presented by Hammond, K. E. et al., "Development of a robust method for generating 7.0 T multichannel phase images of the brain with application to normal volunteers and patients with neurological diseases", NeuroImage 2008, 39; pp. 1682-1692, suggests to estimate a spatially constant phase offset by setting the phase values to zero in all coils at the centre of an image. This method, while being easy to apply, results in areas of poor phase matching.

An alternative solution is to refer the phase values of each receiver coil to a "virtual reference coil" which is the result of a two-step procedure. In the first step, a combined image (the Virtual Reference Coil, or VRC, image) is generated using an image-based constant (as in the method of Hammond et al.). In the second step, the phase image from each coil is referenced to the VRC image. While the matching of phase values of different receiver coils is very good in this case, the method cannot separate the phase offset and magnetic inhomogeneity-related contributions to the total phase.

According to yet another solution Robinson, S. et al., "Combining phase images from multi-channel RF coils using 3D phase offset maps derived from a dual-echo scan", Magn Reson Med 2011, 65; pp. 1638-1648, propose to unwrap the first and second phase images, acquired at the first and the second echo time, respectively, and calculate a phase difference image therefrom. The phase difference image is then unwrapped and added to the unwrapped first phase image to yield an estimate of the phase at the second echo time. By the differences between said estimate and the acquired second phase image, further wraps are identified and the first and the second phase images are further unwrapped to calculate the phase offsets for each coil therefrom. While this method achieves very high SNR and contrast, computing time and storage requirements are also high due to (repeated) unwrapping.

BRIEF SUMMARY

It is an object of the disclosed subject matter to provide a method for determining phase offsets in Magnetic Resonance Imaging which does not rely on an additional volume coil (e.g. body coil) or coarse estimations and yields both efficiency and accuracy.

This objective is achieved with a method for determining phase offsets in a complex-valued image acquired with a receiver coil at an echo time following an excitation by a transmitter coil in Magnetic Resonance Imaging, each pixel of said image representing a volume element of a 3-dimensional object, comprising:

immobilising the object and acquiring a first image of the object at a predetermined first echo time, the first image being separated into a first magnitude image and a first phase image, and a second image of the object at a predetermined second echo time, the second image being separated into a second magnitude image and a second phase image, wherein a ratio between said first echo time and said second echo time is chosen to be n:(n+1), n being a positive integer;

generating, pixel by pixel, a phase evolution image representing phase changes from the first phase image to the second phase image; and subtracting, pixel by pixel, an n-fold of the phase evolution image from the first phase image to obtain a phase offset image containing said phase offsets.

Phase images are conceptually ambiguous because the encoding range in captured phase values is effectively limited to $2\pi$ radians, as adding $2\pi$ to the phase value results in the same measured phase value. Hence, when phase values pass through $2\pi$ the phase image shows discontinuities known as "phase wraps". Therefore, to determine the phase offset unambiguously, it is generally required to unwrap acquired phase images first. However, the present method allows the phase offset image to be determined unambiguously without unwrapping of phase images and even without determining the number or the location of wraps.

The phase offset image will, in general, also contain wraps due to said limitation to $2\pi$ radians. However, these discontinuities do not add up and therefore do not lead to additional ambiguities. This is due to the integer n and the resultant ratio between said first echo time and said second echo time on the one hand and the phase values which generally evolve linearly with echo time after excitation on the other hand. Hence, the present method is particularly efficient in determining the phase offset image.

Favourably, the method further comprises:

subtracting, pixel by pixel, the phase offset image from a phase image acquired with said receiver coil to obtain an offset-corrected phase image.

The offset-corrected phase image corresponds to a phase image acquired with said receiver coil without phase offsets, i.e., without spatially constant components or spatially variable components thereof. Hence, the offset-corrected phase image can be compared to or used with other offset-corrected phase images of the same object, as will be shown in greater detail below.

To enhance the SNR, the phase offset image is optionally smoothed spatially prior to subtracting the phase offset image from the phase image to be offset-corrected. Smoothing the phase offsets reduces noise without removing useful information because the phase offsets vary slowly in space, i.e., they possess only low spatial frequencies. All higher spatial frequencies present in phase offsets are either noise or measurement artefacts. These can be removed by smoothing, as known to the skilled person, to avoid noise being introduced into the offset-corrected phase images. In the simplest case, smoothing can be achieved by generating a moving average over a particular window width of the acquired data. More sophisticated smoothing can be achieved by convolving the image with a smoothing "kernel", e.g. a Gaussian kernel. Smoothing can alternatively be performed by application of a low-pass filter function in the frequency domain, which is linked to the image domain by the Fourier transform.

If the echo times for acquiring a measurement image can be selected without other limitations, it is advantageous when said phase image to be offset-corrected is said first or said second phase image. Acquisition time and memory space for further images can thereby be saved.

However, the phase offset image obtained from the first phase image and the phase evolution image can additionally or alternatively be used to generate an offset-corrected phase image for an image acquired of the immobilised object at any arbitrary echo time deviating from said first and second echo times, e.g., due to possible external restrictions.

The first and second phase images may be acquired at a pixel resolution which differs from the pixel resolution at which said phase image to be offset-corrected is acquired. In a favourable variant, said phase image to be offset-corrected is acquired at a higher pixel resolution than said phase offset image, and said phase offset image is upscaled to said higher pixel resolution prior to offset-correcting said phase image. In other words, the first and second images can be acquired at a lower pixel resolution than said phase image to be offset-corrected. Phase offsets vary slowly in space. Hence, an offset-corrected phase image of high accuracy can be achieved by appropriately upscaling a lower resolution phase offset image. Moreover, the acquisition time for the lower resolution first and second images as well as the memory space for saving the images and the computing time for determining the phase offset image is drastically reduced. Thereby, the determination of the phase offset image can, e.g., be executed on the immobilised object like a quick calibration step preceding a more extensive examination which is conducted at high resolution, based on images acquired at a single echo time or multiple echo times which are independent of said first and second echo times and may follow a separate excitation from the transmitter coil.

In another embodiment, the method is applied to each of a plurality of receiver coils arranged around said immobilised object, wherein, for all receiver coils, a common phase evolution image is generated, the n-fold of which is subtracted from the first phase image of each receiver coil to obtain the phase offset image for said receiver coil. A common transmitter coil could thus be used for excitation of the object while no additional body or volume reference coils are required. By generating such a common phase evolution image both computing time and memory space can be saved, decreasing the duration and the cost of MRI examinations.

In practice, phase evolution is mostly equal for one and the same volume element even when the respective pixel thereof is acquired with different receiver coils. Hence, according to a first variant of the present method, said common phase evolution image is generated by subtracting, pixel by pixel, the first phase image of a predetermined one of said receiver coils from the second phase image of said predetermined receiver coil. No other phase evolution images have to be generated for the remaining other receiver coils in this embodiment. This results in a very quick and simple method of generating the common phase evolution image.

Alternatively, said common phase evolution image is generated as an average of a plurality of phase evolution images each of which having been generated by subtracting, pixel by pixel, the first phase image of one receiver coil of said plurality from the second phase image of said one receiver coil. Thereby, the effects of noise and measurement artefacts which are randomly included in the signals captured by the receiver coils arranged at different positions around the immobilised object are reduced. Numerous algorithms for averaging, all well-known to the skilled person, can be applied.

According to a further alternative variant said common phase evolution image is generated according to:

$$\Delta \vartheta = \angle \left( \sum_c m_{1,c} \cdot m_{2,c} \cdot e^{i(\vartheta_{2,c} - \vartheta_{1,c})} \right)$$

with
- $m_{1,c}, \vartheta_{1,c}$ being the magnitude and phase values of a pixel of the first image acquired with the $c^{th}$ receiver coil,
- $m_{2,c}, \vartheta_{2,c}$ being the magnitude and phase values of the respective pixel of the second image acquired with the $c^{th}$ receiver coil,
- $\Delta \vartheta$ being the value of the respective pixel of the common phase evolution image, and
- $\angle(\bullet)$ denoting the angle operator.

In this variant, both the required computing time and the memory space are lowered as no further phase evolution images have to be generated. Using the magnitude values of the first and second magnitude images, respectively, for weighting the respective phase values of the first and second phase images leads to a low-noise common phase evolution image, as the magnitude values are good estimations of each coil's sensitivity at the respective pixel. However, other weighting factors reflecting said sensitivity could alternatively or additionally be used.

According to a particularly advantageous embodiment, the method further comprises:

obtaining a combined phase image for all receiver coils as a combination of a plurality of offset-corrected phase images, each of which having been acquired of the immobilized object with one of the receiver coils at the same echo time.

The combining is simple as the phase images used are already offset-corrected; moreover, the combined phase image obtained by this combination of offset-corrected phase images of all coils is low-noise. For each echo time, a separate combined phase image can be obtained the same way.

A particularly low-noise combined phase image can be achieved, when said combined phase image is obtained according to $$\vartheta_{k,F} = \angle \left( \sum_c m_{k,c} \cdot e^{i\vartheta'_{k,c}} \right)$$

with
- k being an index of said echo time,
- $m_{k,c}$ being the magnitude value of a pixel of the $k^{th}$ image acquired with the $c^{th}$ receiver coil,
- $\vartheta'_{k,c}$ being the offset-corrected phase value of the respective pixel of the $k^{th}$ offset-corrected phase image of the $c^{th}$ receiver coil,
- $\vartheta'_{k,F}$ being the value of the respective pixel in the $k^{th}$ combined phase image, and
- $\angle(\bullet)$ denoting the angle operator.

The low-noise, high SNR combined phase image is obtained as a consequence of weighting the offset-corrected phase value of each pixel by the magnitude value of the respective pixel. As mentioned previously, other weighting factors, particularly weighting factors reflecting the sensitivity of each coil at the respective pixel, could additionally or alternatively be deployed.

For decreasing the acquisition and examination time, it is favourable when the respective images acquired with said plurality of receiver coils are all acquired following one and the same excitation.

BRIEF DESCRIPTION OF THE DRAWINGS/FIGURES

The disclosed subject matter will now be described in further details by means of exemplary embodiments thereof under reference to the enclosed drawings, in which.

DETAILED DESCRIPTION

Magnetic Resonance Imaging (MRI) is used in radiology to visualize soft tissues, non-invasively and in vivo. The process of generating an image of a patient usually consists of the following steps: creating a bulk (longitudinal) magnetisation in the tissue by placing and immobilising the patient inside a powerful static magnetic field; creating regional variation in this magnetic field, and thereby in the resonant frequency and phase of the nuclei, with three comparatively small, linear perpendicular magnetic fields ("gradients"); disturbing the magnetisation with one or more pulses of radio-frequency (RF) electromagnetic radiation ("excitation") applied at the resonant frequency by one or more transmitter coils, tipping the magnetisation into the transverse plane (which is perpendicular to the static magnetic field); and acquiring the RF signals emitted by the tissues as the magnetisation relaxes to the longitudinal direction, by one or more receiver coils.

In 2-dimensional tomographic imaging, space encoding of the signal works as follows. The first gradient field ("slice select") is applied during RF excitation, so that only spins in a narrow section of tissue are excited. The second ("readout") is applied while the signal is being acquired, so that spins along the readout axis are encoded by their resonant frequency. A number of such excitation-readout steps are acquired with differing applications of the third ("phase-encode") gradient, which encodes the signal along that gradient direction according to a dephasing rate. In 3-dimensional imaging, slice encoding is replaced by a second loop of phase-encoding steps in the slice gradient direction.

The RF signals emitted by the patient are captured as "echoes" at a certain time (the "echo time") after excitation, by one or more receiver coils arranged around the immobilised patient. Fourier-transforming the acquired MR-signals generates images of the patient, which consist of a large number of pixels representing volume elements, reflecting the local proton density and magnetic properties of the tissue. The acquired MR signals are complex-valued; images of the patient, as the Fourier-transform of the acquired signal, are therefore likewise complex-valued. That is, image signals consist of a magnitude value and a phase value and can be represented in conventional complex number notation. While the magnitude value of the signal decays exponentially with echo time, the phase value evolves linearly and reflects local deviation from the main magnetic field strength.

Some MRI methods use only the magnitude of the MR-signal. Nevertheless, the phase value contains additional information, which can be clinically useful. The sensitivity of phase to local magnetic field, for instance, allows local iron (which is highly paramagnetic) to be imaged. Phase values can be used in combination with magnitude values, e.g., to depict veins, due to the iron content of the deoxy-hemoglobin iron, in a technique known as Susceptibility-Weighted Imaging. These techniques benefit from a high static magnetic field, which provides enhanced magnetic susceptibility effects and higher quality images due to increased signal-to-noise ratio (SNR).

Figure 1:
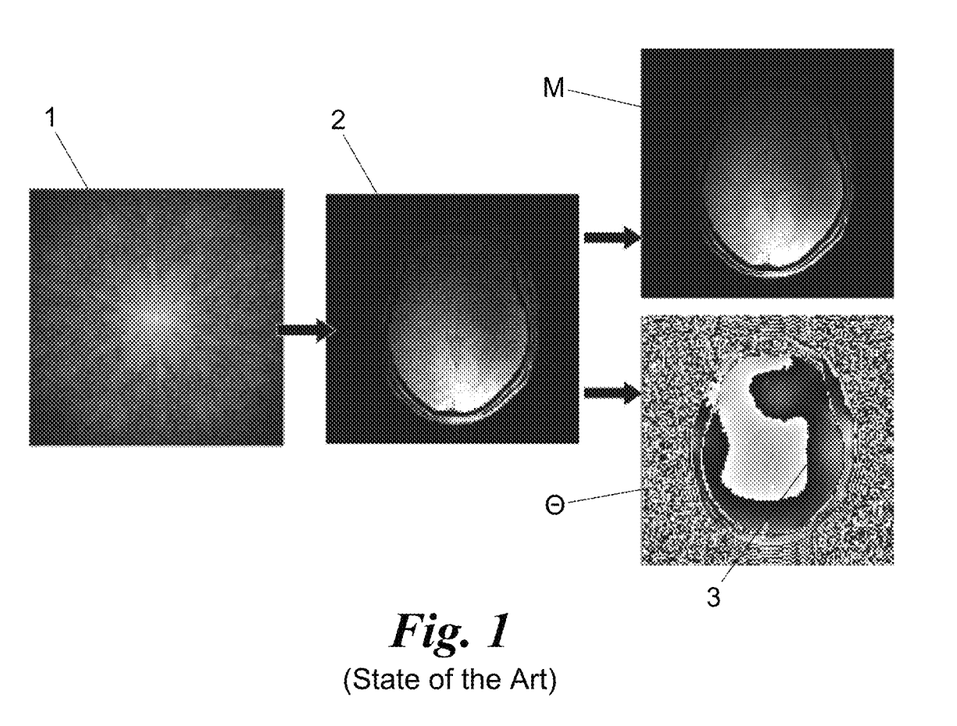
FIG. 1 shows the generation of a complex-valued image in Magnetic Resonance Imaging according to the state of the art.

As shown in FIG. 1, captured signals of an acquired complex-valued signal image 1 of an object to be examined cannot be interpreted straightforwardly. Fourier-transforming image 1 results in a complex-valued image 2 which can be separated on a pixel-by-pixel basis into a magnitude image M and a phase image $\Theta$, as each complex value is a vector in the complex plane with a magnitude and a phase (angle). In this context, said separation does not necessarily require an additional distinct procedural step but, more generally, denotes a separate consideration of the magnitude values of the image 2 on the one hand and its phase values on the other.

However, the phase image $\Theta$ suffers from a conceptual ambiguity: As adding $2\pi$ to the phase of a signal results in the same measured phase value, the encoding range in captured phase values is effectively limited to $2\pi$ radians. Variations in phase values of an object when passing through $2\pi$ lead to discontinuities in the phase image $\Theta$ known as "phase wraps" 3, which distort the readability and obscure interesting phase features.

Moreover, the phase values of the phase image $\Theta$ contain a time-independent phase offset, which, inter alia, depends on the position of the receiver coil of the MRI machine relative to the object to be examined and, to a certain extent, on the individual volume element to be examined because it is determined by the MR wavelength in the medium being imaged, which depends on the electrical conductivity and permittivity. Phase images acquired by different receiver coils which generally are arranged as phased array coil elements around the 3-dimensional object can therefore not be combined with ease.

With reference to FIGS. 2 to 5, different embodiments of an MRI method for determining and, optionally, also accommodating these phase offsets shall now be described.

Figure 2:
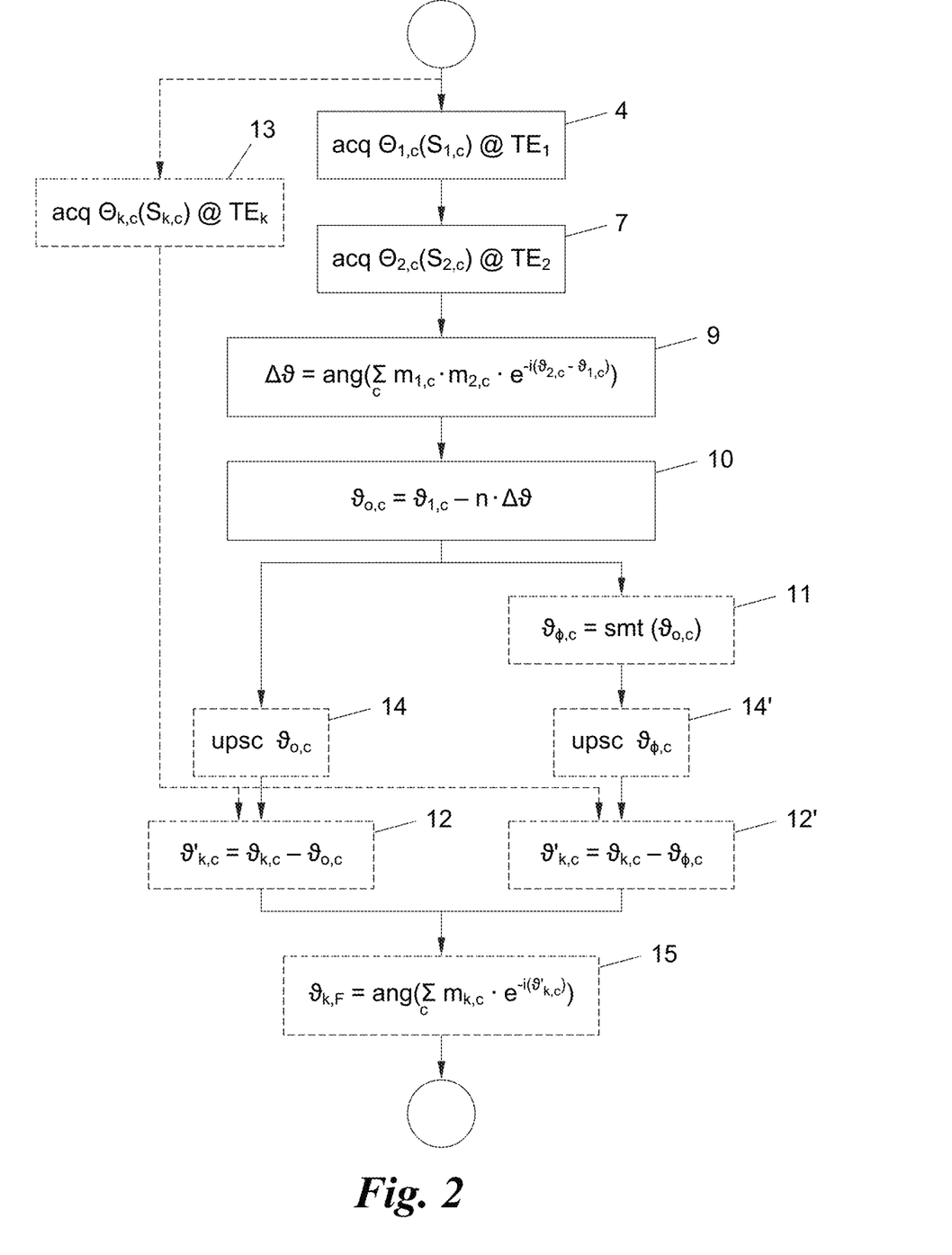
FIG. 2 shows a flow chart of different embodiments of the method of the disclosed subject matter.
Figure 3:
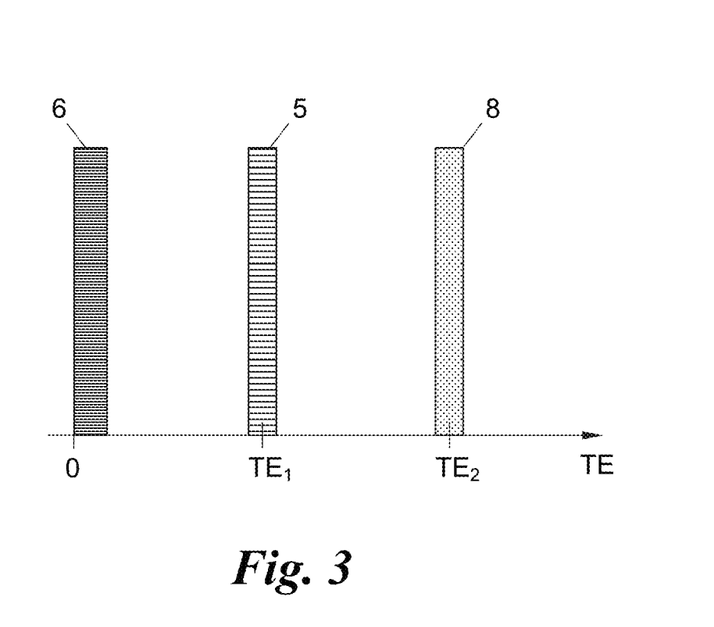
FIG. 3 depicts a timing diagram of an exemplary acquisition cycle used in the method of FIG. 2.

According to FIG. 2 in a first step 4 of said method a first image $S_1$ of the object, here: the first image $S_{1,c}$ of an exemplary receiver coil from a multitude of receiver coils with indices c=1, 2, 3, . . . of the MRI machine, is acquired at a predetermined first echo time $TE_1$ (FIG. 3).

As can be seen from the schematic representation of FIG. 3, acquiring each first image $S_{1,c}$ takes a certain, finite acquisition period 5; similarly, the excitation at TE=0 is conducted by a pulse 6 of finite length. The excitation could alternatively be conducted by a predefined series of pulses, each pulse 6 for acquiring one or more volume elements step-by-step. Any excitation, whether a single pulse or a series of pulses, may be generated by a single or a plurality of transmitter coils, as known in the art.

Said first images $S_{1,1}$, $S_{1,2}$, . . . , generally $S_{1,c}$, are—as a Fourier-transform of complex measured data—complex-valued, similarly to the image 2 of FIG. 1. Each of the complex-valued first images $S_{1,c}$ can therefore be separated into a first magnitude image (not shown) and a first phase image $\Theta_{1,c}$ (FIG. 4a), in which the volume elements of the object are represented by complex-valued pixels comprising each a first magnitude value $m_{1,c}$ and a first phase value $\vartheta_{1,c}$, respectively. For better readability, both the magnitude values $m_{1,c}$ and the phase values $\vartheta_{1,c}$, albeit being pixel-specific, are written herein without an index for the respective pixel (cf. FIG. 2).

Reverting to FIG. 2, in a step 7—which can be performed using the same excitation pulse 6 or pulses as in step 4, or using a different excitation pulse 6 or pulses—a second image $S_2$ of the object (here: the target image $S_{2,c}$ of the receiver coil with index c) is acquired at a predetermined second echo time $TE_2$ over a finite acquisition period 8 (FIG. 3), while keeping the object immobilised with respect to step 4. The second image $S_{2,c}$ is likewise separated into a second magnitude image (not shown) and a second phase image $\Theta_{2,c}$ (FIG. 4a), wherein each pixel reflects a second magnitude value $m_{2,c}$ or a second phase value $\vartheta_{2,c}$, respectively.

According to the present method, the first echo time $TE_1$ and the second echo time $TE_2$ are chosen with a mutual ratio $TE_1:TE_2=n:(n+1)$, n being an arbitrary positive integer. In the simplest case (depicted in the example of FIG. 3), the integer n equals "1", resulting in the second echo time $TE_2$ being twice the first echo time $TE_1$.

In a following step 9, a phase evolution image $\Delta\Theta$ (FIG. 4b) is generated, pixel by pixel. There are several ways of generating the phase evolution image $\Delta\Theta$ as will be exemplified in greater detail below. In any case, the phase evolution image $\Delta\Theta$ represents phase changes from the first phase image $\Theta_{1,c}$ to the second phase image $\Theta_{2,c}$. In FIG. 2, the phase evolution value $\Delta\vartheta$ of a pixel in the phase evolution image $\Delta\Theta$ is again shown without an index for the respective pixel.

Figure 4A:
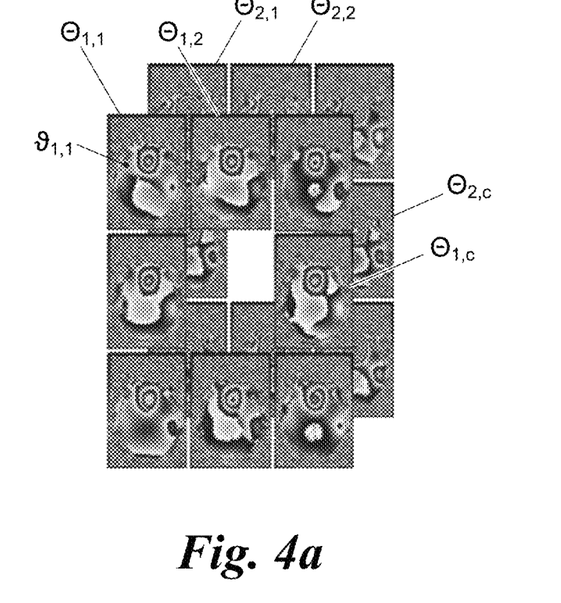
FIGS. 4a to 4d depict examples of phase images acquired (FIG. 4a) and of a phase evolution image (FIG. 4b), phase offset images (FIG. 4c) and smoothed phase offset images (FIG. 4d) obtained according to the method of FIG. 2.
Figure 4B:
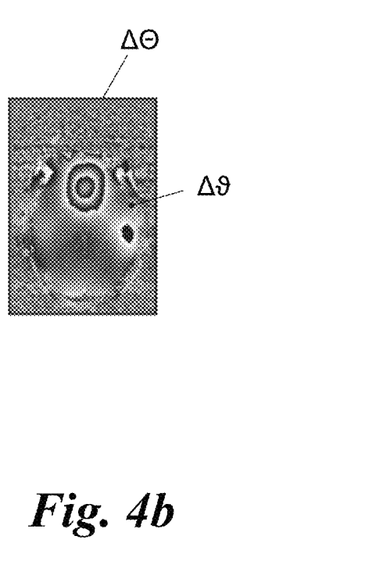
Figure 4C:
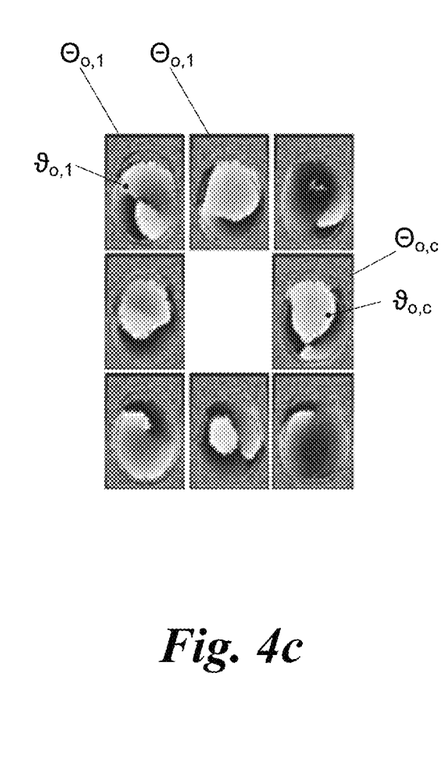
Figure 4D:
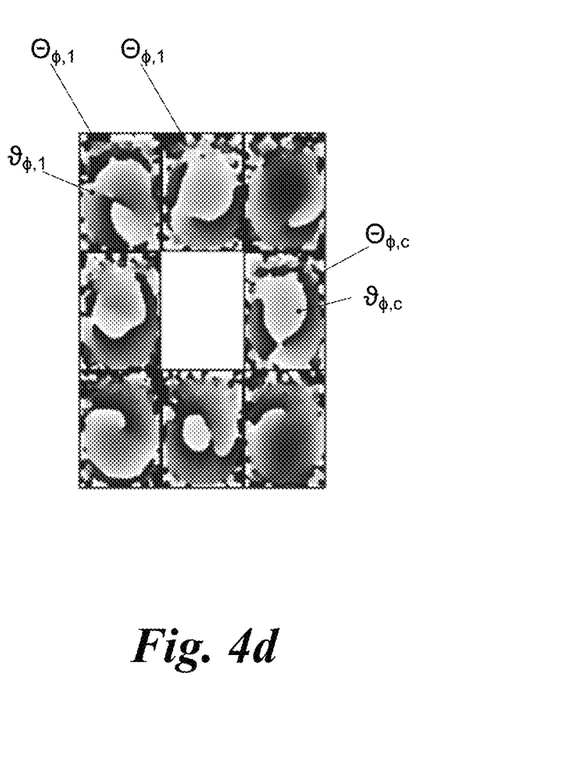

Thereafter, a phase offset image $\Theta_o$ (here: the phase offset image $\Theta_{o,c}$ of the receiver coil with index c) containing said phase offsets $\vartheta_{o,c}$ is obtained in step 10 by subtracting, pixel by pixel, an n-fold of the phase evolution image $\Delta\Theta$, i.e., the phase evolution image $\Delta\Theta$ is multiplied, pixel by pixel, by said integer n and then subtracted from the first phase image $\Theta_{1,c}$. The result is shown in FIG. 4c.

By subtracting the n-fold of the phase evolution image $\Delta\Theta$ from the first phase image $\Theta_{1,c}$, the first phase values $\vartheta_{1,c}$ are, in essence, scaled back to the excitation time (TE=0) due to the linear evolvement of phase values. However, by choosing said ratio between the first echo time $TE_1$ and the second echo time $TE_2$ ($TE_1$:$TE_2$) to be n:(n+1), the resulting phase offset image $\Theta_{o,c}$, while in general still having wraps, is highly accurate without determining the number or the location of the wraps and without prior unwrapping.

In an optional step 11, the phase offset image $\Theta_{o,c}$ can be smoothed spatially. As phase offsets vary slowly in space, they possess only low spatial frequencies; all higher spatial frequencies present in phase offsets are either noise or measurement artefacts, which are removed or at least reduced by smoothing. As known to the skilled person, smoothing can be achieved, e.g., by generating a moving average over a particular window of the acquired image (here: the phase offset image $\Theta_{o,c}$) or by convolving the image with a smoothing "kernel", e.g. a Gaussian kernel. Smoothing can alternatively be performed in the frequency domain—linked to the image domain by the Fourier transform—e.g., by application of a low-pass filter function. Spatial smoothing of the phase values is applied in complex number space (i.e., to real and imaginary parts) to avoid causing errors due to wraps (which are high frequency features).

The smoothed phase offset image $\Theta_{\phi,c}$ (FIG. 4d) or the smoothed phase offset values $\epsilon_{\phi,c}$ of the pixels thereof can be used instead of the phase offset image $\Theta_{o,c}$ in further processing.

Figure 5A:
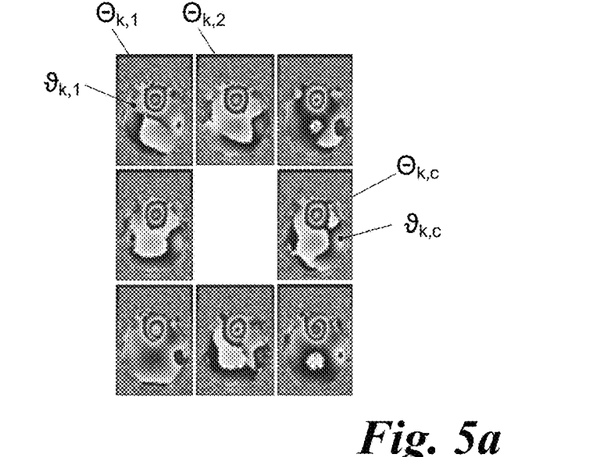
FIGS. 5a to 5c depict examples of phase images acquired (FIG. 5a) and of offset-corrected phase images (FIG. 5b) and combined phase images (FIG. 5c) obtained according to the method of FIG. 2.

If desired, the phase offset image $\Theta_{o,c}$ is subtracted, pixel by pixel, from said first phase image $\Theta_{1,c}$ and/or said second phase image $\Theta_{2,c}$, respectively, acquired with said receiver coil with index c to obtain an offset-corrected phase image $\Theta'_{1,c}$ and/or $\Theta'_{2,c}$, respectively, cf. step 12 in FIG. 2 and FIG. 5a.

It shall be understood that the present method is not limited to obtaining offset-corrected phase images $\Theta'_{1,c}$, $\Theta'_{2,c}$ of the first and/or second phase images $\Theta_{1,c}$, $\Theta_{2,c}$. It can similarly be applied to any other phase image $\Theta_{1,c}$, $\Theta_{2,c}$, . . . , generally $\Theta_{k,c}$, acquired of the immobilised object with the same receiver coil with index c at different echo times $TE_1$, $TE_2$, . . . , generally $TE_k$, to obtain respective offset-corrected phase images $\Theta'_{1,c}$, $\Theta'_{2,c}$, . . . , generally $\Theta'_{k,c}$. Optional step 13 in FIG. 2 symbolises the acquisition of further images $S_{k,c}$. However, for any offset-corrected phase image $\Theta'_{k,c}$ the phase offset image $\Theta_{o,c}$—or the smoothed phase offset image $\Theta_{\phi,c}$, respectively—is generated by means of the first and second phase images $\Theta_{1,c}$, $\Theta_{2,c}$.

If desired, some of the phase image(s) $\Theta_{k,c}$ (apart from the first and second phase images $\Theta_{1,c}$, $\Theta_{2,c}$) may be acquired at a different (here: a higher) pixel resolution than said first and second phase images $\Theta_{1,c}$, $\Theta_{2,c}$, and consequently than said phase offset image $\Theta_{o,c}$, in which case the phase offset image $\Theta_{o,c}$ is scaled (here: upscaled) to said higher pixel resolution in step 14 prior to offset-correcting the respective phase image $\Theta_{k,c}$—or the phase values $\vartheta_{k,c}$—in step 12. Some phase image(s) $\vartheta_{k,c}$ could, optionally, be acquired with a different geometry than said first and second phase images $\Theta_{1,c}$, $\Theta_{2,c}$, i.e., a different orientation, field of view or coverage of the object; in this case, respective pixels are selected from the phase offset image $\Theta_{o,c}$ as required, e.g. from different "slices" thereof, and, when necessary, scaled for offset-correcting said phase images $\Theta_{k,c}$.

Figure 5B:
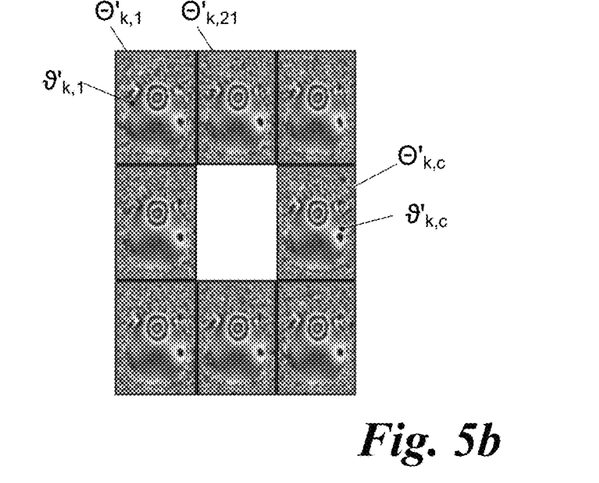
Figure 5C:
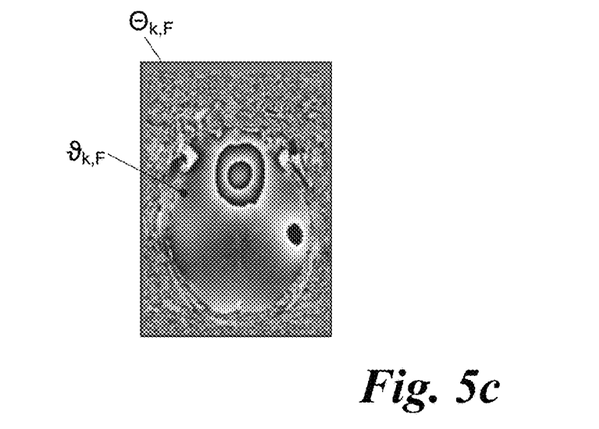

In case of smoothing the phase offset image $\Theta_{o,c}$ in step 11, said smoothed phase offset image $\Theta_{\phi,c}$ can be subtracted, pixel by pixel, from the phase image $\Theta_{k,c}$ acquired with said receiver coil (index c) in step 12' to obtain the offset-corrected phase image $\Theta'_{k,c}$ (FIG. 5b). If necessary, the smoothed phase offset image $\Theta_{\phi,c}$, prior to step 12', is upscaled to the higher pixel resolution of the phase image $\Theta_{k,c}$ in step 14' of FIG. 2.

As indicated by the receiver coil index c, the present method can either be applied to the phase image $\Theta_{k,c}$ of a single receiver coil or, similarly, to each of a plurality of receiver coils arranged around said immobilised object. In the latter case, a common phase evolution image $\Delta\Theta$ may be generated for some or all receiver coils, whereupon the n-fold of the common phase evolution image $\Delta\Theta$ is subtracted from the first phase image $\Theta_{1,c}$ of each receiver coil to obtain the phase offset image $\Theta_{o,c}$ for said receiver coil. Said phase offset image $\Theta_{o,c}$ can optionally be smoothed to obtain and further utilize a smoothed phase offset image $\Theta_{\phi,c}$ as exemplified above.

The common phase evolution image $\Delta\Theta$ can be generated in variety of ways. One exemplary way of generating said common phase evolution image $\Delta\Theta$ is by subtracting, pixel by pixel, the first phase image $\Theta_{1,c}$ of a predetermined one of said receiver coils from the second phase image $\Theta_{2,c}$ of said predetermined receiver coil. The resulting phase evolution image $\Delta\Theta$ is then used as the common phase evolution image $\Delta\Theta$ for subtracting the n-fold thereof from the first phase image $\Theta_{1,c}$ of each receiver coil to obtain the phase offset image $\Theta_{o,c}$ for said receiver coil.

According to another variant, said common phase evolution image $\Delta\Theta$ is generated as an average of a plurality of phase evolution images each of which has been generated by subtracting, pixel by pixel, the first phase image $\Theta_{1,c}$ of one receiver coil of said plurality from the second phase image $\Theta_{2,c}$ of said one receiver coil. There is a multitude of algorithms for averaging which can fruitfully be used and one of which can easily be selected by the skilled person. While usually desired, it is not necessary to generate the common phase evolution image $\Delta\Theta$ as an average of the phase evolution images of all receiver coils but only of some of them.

The variant depicted in step 9 of FIG. 2 suggests to generate said common phase evolution image $\Delta\Theta$ according to:

$$\Delta\vartheta = \angle\left(\sum_c m_{1,c} \cdot m_{2,c} \cdot e^{i(\vartheta_{2,c} - \vartheta_{1,c})}\right) \quad \text{(eq. 1)}$$

with
- $m_{1,c}$, $\vartheta_{1,c}$ being the magnitude and phase values of a pixel of the first image $S_{1,c}$ acquired with the $c^{th}$ receiver coil,
- $m_{2,c}$, $\vartheta_{2,c}$ being the magnitude and phase values of the respective pixel of the second image $S_{2,c}$ acquired with the $c^{th}$ receiver coil,
- $\Delta\vartheta$ being the value of the respective pixel of the common phase evolution image $\Delta\Theta$, and
- $\angle(\bullet)$ denoting the angle operator which can, e.g., be implemented as a four-quadrant tangent inverse operation, also known as "a tan 2"-function in trigonometry.

In this way, the phase values $\vartheta_{1,c}$, $\vartheta_{2,c}$ of the first and the second phase images $\Theta_{1,c}$, $\Theta_{2,c}$, respectively, are not only subtracted from each other but weighted with the respective magnitude values $m_{1,c}$, $m_{2,c}$ of the first and second magnitude images of the respective receiver coil (index c). Thereby, a low-noise common phase evolution image $\Delta\Theta$ is obtained. However, other weighting factors, e.g., factors which reflect the sensitivity of the respective receiver coil at the respective pixel (as the magnitude values $m_{1,c}$, $m_{2,c}$ do), could additionally or alternatively be used, or, when higher noise levels are acceptable, weighting factors could even be skipped, i.e., set to "1" in eq. 1.

The present method may further comprise obtaining a combined phase image $\Theta_{k,F}$ (FIG. 5c) for all receiver coils as a combination of a plurality of offset-corrected phase images $\Theta'_{k,c}$, each of which has been acquired of the immobilized object with one of the receiver coils at the same, i.e., the k-th echo time $TE_k$, as depicted by step 15 of FIG. 2. The combined phase image $\Theta_{k,F}$ may be obtained from the offset-corrected phase images $\Theta'_{k,c}$ of some or of all receiver coils.

In general, the combined phase image $\Theta_{k,F}$ is obtained by calculating, pixel by pixel, combined phase values $\vartheta_{k,F}$ as an angle of a complex sum of the offset-corrected phase values $\vartheta'_{k,c}$ of the receiver coils. During this calculation, the offset-corrected phase values $\vartheta'_{k,c}$ may optionally be weighted by a suitable weighting factor reflecting the sensitivity of the respective receiver coil at the respective pixel (or volume element of the object). A suitable weighting factor is—again—the magnitude value $m_{k,c}$ of the respective pixel. Hence, said combined phase image is optionally obtained according to $$\vartheta_{k,F} = \angle\left(\sum_c m_{k,c} \cdot e^{i\vartheta'_{k,c}}\right) \quad \text{(eq. 2)}$$

with k being an index of said echo time, $m_{k,c}$ being the magnitude value of a pixel of the $k^{th}$ image acquired with the $c^{th}$ receiver coil, $\vartheta'_{k,c}$ being the offset-corrected phase value of the respective pixel of the $k^{th}$ offset-corrected phase image of the $c^{th}$ receiver coil, $\vartheta_{k,F}$ being the value of the respective pixel in the $k^{th}$ combined phase image, and $\angle(\bullet)$ denoting the angle operator.

The first or second echo time $TE_1$, $TE_2$ and/or other echo times $TE_k$ may follow the same excitation for some or all receiver coils, i.e., some or all of the respective images $S_{1,c}$, $S_{2,c}$, . . . , generally $S_{k,c}$, acquired with said plurality of receiver coils following one and the same excitation by the transmitter coil. Alternatively, a separate excitation for each echo time $TE_1$, $TE_2$, $TE_k$ and/or different receiver coils could be used.

The disclosed subject matter is not limited to the embodiments described in detail above, but encompasses all variants, modifications and combinations thereof which will become apparent to the person skilled in the art from the present disclosure and which fall into the scope of the appended claims.

What is claimed is:

1. A method for determining phase offsets in a complex-valued image acquired with a receiver coil at an echo time following an excitation by a transmitter coil in Magnetic Resonance Imaging, each pixel of said image representing a volume element of a 3-dimensional object, comprising:

immobilising the object and acquiring a first image of the object at a predetermined first echo time, the first image being separated into a first magnitude image and a first phase image, and a second image of the object at a predetermined second echo time, the second image being separated into a second magnitude image and a second phase image, wherein a ratio between said first echo time and said second echo time is chosen to be n:(n+1), n being a positive integer;

generating, pixel by pixel, a phase evolution image representing phase changes from the first phase image to the second phase image; and subtracting, pixel by pixel, an n-fold of the phase evolution image from the first phase image to obtain a phase offset image containing said phase offsets.

2. The method of claim 1, further comprising:

subtracting, pixel by pixel, the phase offset image from a phase image acquired with said receiver coil to obtain an offset-corrected phase image.

3. The method of claim 2, wherein, prior to subtracting the phase offset image from the phase image to be offset-corrected, the phase offset image is smoothed spatially.

4. The method of claim 2, wherein said phase image to be offset-corrected is said first or said second phase image.

5. The method of claim 2, wherein said phase image to be offset-corrected is acquired at a higher pixel resolution than said phase offset image, and said phase offset image is upscaled to said higher pixel resolution prior to offset-correcting said phase image.

6. The method of claim 1 applied to each of a plurality of receiver coils arranged around said immobilised object, wherein, for all receiver coils, a common phase evolution image is generated, the n-fold of which is subtracted from the first phase image of each receiver coil to obtain the phase offset image for said receiver coil.

7. The method of claim 6, wherein said common phase evolution image is generated by subtracting, pixel by pixel, the first phase image of a predetermined one of said receiver coils from the second phase image of said predetermined receiver coil.

8. The method of claim 6, wherein said common phase evolution image is generated as an average of a plurality of phase evolution images each of which having been generated by subtracting, pixel by pixel, the first phase image of one receiver coil of said plurality from the second phase image of said one receiver coil.

9. The method of claim 6, wherein said common phase evolution image is generated according to:

$$\Delta\vartheta = \angle\left(\sum_c m_{1,c} \cdot m_{2,c} \cdot e^{i(\vartheta_{2,c} - \vartheta_{1,c})}\right)$$

with $m_{1,c}$, $\vartheta_{1,c}$ being the magnitude and phase values of a pixel of the first image acquired with the $c^{th}$ receiver coil, $m_{2,c}$, $\vartheta_{2,c}$ being the magnitude and phase values of the respective pixel of the second image acquired with the $c^{th}$ receiver coil, $\Delta\vartheta$ being the value of the respective pixel of the common phase evolution image, and $\angle(\bullet)$ denoting the angle operator.

10. The method of claim 6, further comprising:

obtaining a combined phase image for all receiver coils as a combination of a plurality of offset-corrected phase images, each of which having been acquired of the immobilized object with one of the receiver coils at the same echo time.

11. The method of claim 10, wherein said combined phase image is obtained according to $$\vartheta_{k,F} = \angle\left(\sum_c m_{k,c} \cdot e^{i\vartheta'_{k,c}}\right)$$

with
- k being an index of said echo time,
- $m_{k,c}$ being the magnitude value of a pixel of the $k^{th}$ image acquired with the $c^{th}$ receiver coil,
- $\vartheta_{k,c}'$ being the offset-corrected phase value of the respective pixel of the $k^{th}$ offset-corrected phase image of the $c^{th}$ receiver coil,
- $\vartheta_{k,F}$ being the value of the respective pixel in the $k^{th}$ combined phase image, and
- $\angle(\bullet)$ denoting the angle operator.

12. The method of claim 6, wherein the respective images acquired with said plurality of receiver coils are all acquired following one and the same excitation.

* * * * *